United States Patent
Ferry et al.

(10) Patent No.: US 11,998,624 B2
(45) Date of Patent: Jun. 4, 2024

(54) ANHYDROUS ANTIPERSPIRANT AEROSOL COMPOSITION

(71) Applicant: Conopco, Inc., Englewood Cliffs, NJ (US)

(72) Inventors: Anne-Laure Sophie Ferry, Liverpool (GB); Robert Edward Marriott, Merseyside (GB); Louise Jannette Roberts, Merseyside (GB)

(73) Assignee: CONOPCO, INC., Englewood Cliffs, NJ (US)

( * ) Notice: Subject to any disclaimer, the term of this patent is extended or adjusted under 35 U.S.C. 154(b) by 54 days.

(21) Appl. No.: 16/640,594

(22) PCT Filed: Aug. 9, 2018

(86) PCT No.: PCT/EP2018/071689
§ 371 (c)(1),
(2) Date: Feb. 20, 2020

(87) PCT Pub. No.: WO2019/038101
PCT Pub. Date: Feb. 28, 2019

(65) Prior Publication Data
US 2020/0170893 A1 Jun. 4, 2020

(30) Foreign Application Priority Data

Aug. 23, 2017 (EP) .................................. 17187442

(51) Int. Cl.
*A61K 8/04* (2006.01)
*A61K 8/26* (2006.01)
*A61K 8/42* (2006.01)
*A61K 8/58* (2006.01)
*A61Q 15/00* (2006.01)

(52) U.S. Cl.
CPC .............. *A61K 8/046* (2013.01); *A61K 8/26* (2013.01); *A61K 8/42* (2013.01); *A61K 8/585* (2013.01); *A61Q 15/00* (2013.01); *A61K 2800/31* (2013.01)

(58) Field of Classification Search
None
See application file for complete search history.

(56) References Cited

U.S. PATENT DOCUMENTS

| | | | |
|---|---|---|---|
| 2,872,379 A | 2/1959 | Neumann et al. | |
| 3,509,253 A | 4/1970 | Babbin | |
| 3,928,557 A | 12/1975 | Wright et al. | |
| 3,981,986 A | 9/1976 | Rubino | |
| 4,108,977 A | 8/1978 | Kenkare et al. | |
| 4,113,852 A * | 9/1978 | Kenkare ................. | A61K 8/26 424/47 |
| 5,162,378 A | 10/1992 | Guthauser | |
| 5,405,605 A | 11/1995 | Shin | |
| 5,518,714 A | 5/1996 | Park | |
| 8,518,384 B2 | 8/2013 | Fletcher et al. | |
| 2005/0008604 A1 | 1/2005 | Schultz et al. | |
| 2007/0036738 A1 | 2/2007 | Fletcher et al. | |
| 2007/0292328 A1 | 12/2007 | Yang et al. | |
| 2009/0257970 A1 * | 10/2009 | Bloom ..................... | A61K 8/19 424/66 |
| 2010/0104611 A1 | 4/2010 | Chan et al. | |
| 2012/0003284 A1 * | 1/2012 | Arnaud ..................... | A61K 8/28 424/401 |
| 2012/0121677 A1 | 5/2012 | Franklin | |
| 2013/0195775 A1 | 8/2013 | Goddard et al. | |
| 2014/0294976 A1 | 10/2014 | Argembeaux et al. | |
| 2014/0314701 A1 | 10/2014 | Pan et al. | |
| 2015/0037264 A1 | 2/2015 | Bellamy | |
| 2015/0283044 A1 * | 10/2015 | Swaile ................... | A61K 8/046 222/394 |
| 2015/0376546 A1 | 12/2015 | Diaz Gomez et al. | |
| 2016/0106649 A1 * | 4/2016 | Fawzy ..................... | A61K 8/44 424/68 |

FOREIGN PATENT DOCUMENTS

| | | | |
|---|---|---|---|
| EP | 0274267 | * | 7/1987 |
| EP | 0272354 | | 6/1988 |
| EP | 0274267 | | 7/1988 |
| EP | 0957897 | | 7/2003 |
| GB | 795222 | | 5/1958 |
| GB | 1534861 | | 12/1978 |
| GB | 2096891 | * | 10/1982 |
| WO | WO2010031657 | | 3/2010 |
| WO | WO2010046291 | | 4/2010 |
| WO | WO2016066528 | | 5/2016 |

OTHER PUBLICATIONS

.; .; Search Report and Written Opinion in PCTEP2018071689; Sep. 28, 2018.
Search Report and Written Opinion in EP17187442; Nov. 21, 2017.
Search Report and Written Opinion in EP16183942; Jan. 2, 2017.
IPRP1 in PCTEP2018071689; Feb. 25, 2020; World Intellectual Property Org. (WIPO).

* cited by examiner

*Primary Examiner* — Tigabu Kassa
(74) *Attorney, Agent, or Firm* — Stephanie Huang

(57) ABSTRACT

Anhydrous antiperspirant aerosol compositions comprising antiperspirant active, urea, non-ethanolic carrier oil and volatile propellant, said compositions delivering good perspiration reduction and humectancy, without valve blockage of associated hardware.

14 Claims, No Drawings

ANHYDROUS ANTIPERSPIRANT AEROSOL COMPOSITION

RELATED APPLICATIONS

This application is a national phase filing under 35 USC 371 of International Application No. PCT/EP2018/071689, filed on Aug. 9, 2018, which claims priority from European Patent Application No. 17187442.3 filed, Aug. 23, 2017, the contents of which are incorporated herein in their entirety for all purposes.

FIELD OF THE INVENTION

The present invention relates to antiperspirant compositions. In particular, the present invention relates to base anhydrous antiperspirant compositions comprising an antiperspirant active, a urea and a non-ethanolic carrier oil, to anhydrous antiperspirant aerosol compositions comprising such base and to their manufacture.

BACKGROUND OF THE INVENTION

Antiperspirant compositions are available from various applicators, of which the aerosol format is particularly popular because it avoids the contact between the applicator and the body. Consequently, the hygiene is improved. An aerosol composition typically comprises a base formulation and a liquefied propellant gas. For the base and for the aerosol composition, anhydrous composition is often preferred because of the desire to avoid an aqueous component causing corrosion of the thin metal wall from the aerosol canister.

It is recognised by the manufacturer that a base formulation needs to present certain viscosity. If it is too thick, the mixing will be difficult (to create a homogeneous base) and a thick base may further block the filing line to the canister. If too thin, the base composition may split and/or cause undesirable splash at mixing as well as filling stage. To the knowledge of the Applicant, there is little prior art providing improvement in this area.

In another aspect of the anhydrous formulation, research conducted on behalf of the Applicant in 1990s recognized the employment of astringent antiperspirant salts such as aluminium tends to cause de-moisturisation of the skin and impairment of skin elasticity. The problem can be ameliorated by incorporation of a humectant into the formulation, which has the ability to absorb water from its surroundings and locking the moisture onto the surface of the skin, making it moist and healthy. One of the best known humectants used in skin care formulation is glycerol (glycerin). Glycerin can be incorporated into aqueous antiperspirant formulations without any issues. However, issues arise while incorporating glycerin into anhydrous antiperspirant formulations due to an interaction between the glycerin and the antiperspirant active itself.

EP 957897 contemplates antiperspirant aerosol composition containing polyol humectant such as glycerol. It has been found that the incorporation of glycerol (and also propylene glycol) tends to increase the weighted average particle size (diameter) of the particles in the composition by increasing the fraction of larger particles, possibly by agglomeration of smaller particles. The outcome is an increased risk of blockage of the outlet nozzle in aerosol applicator. Commonly, the problem of blockage increases significantly as the proportion of particles having a diameter in excess of 125 microns increases. At the same time, compositions containing a significant fraction of particles in the region of 100 microns or higher tend to be unstable as well as exhibiting poor or impaired sensory properties.

U.S. Pat. No. 8,518,384 relates to spray compositions and particularly anhydrous aerosol compositions containing particulate antiperspirant actives exhibit a tendency for nozzle blockage, impeding discharge of the contents when a polyol humectant, such as glycerol, is blended into its base composition. The technical problem in that document is solved by the preparation of a base composition, suitable for employment in conjunction with a propellant that contains a low molecular weight (liquid) polyethylene glycol (PEG) as humectant, and particularly a PEG of molecular weight 150 to 500.

WO10031657 discloses the use of urea derivatives and phenacylthiazolium salts for the inhibition of enzymes, in particular the cystathionine-beta-lyase, and/or for the prevention or treatment of body odour, in particular in the axillary or oral region, and to cosmetic and pharmaceutical preparations, in particular deodorants and antiperspirants containing said active substances.

U.S. Pat. No. 5,518,714 and EP0274267 both dissolve urea in ethanol before mixing with antiperspirant. No blockage issue is reported, however, the use of ethanol is considered irritant to skin.

Although the prior art provides for various solutions to the problem of interaction between the humectant the antiperspirant actives in anhydrous antiperspirant aerosol compositions, improved ways of addressing this problem still remains to be desired.

It is therefore an object of the invention to provide an anhydrous antiperspirant base composition with a viscosity suitable for processing.

It is another object of the present invention to identify a suitable humectant which can be incorporated in an anhydrous antiperspirant base composition suitable for incorporation in an anhydrous aerosol composition, which offers less risk of blockage and product instability.

Herein, "blockage" refers to blockage of the valve stem and/or associated dispenser hardware used to dispense an anhydrous aerosol composition produced from an anhydrous base composition.

It is yet another object of the invention to provide an anhydrous antiperspirant aerosol composition with improved skin sensory benefits. Surprisingly, it has been found that stable, skin-friendly anhydrous antiperspirant aerosol compositions wherein the base composition presents proper viscosity and no agglomeration can be achieved by the use of urea in specific concentrations in the composition.

SUMMARY OF THE INVENTION

In a first aspect, the present invention provides an anhydrous antiperspirant aerosol composition with less than 1% by weight of free water of the total composition, comprising: (i) 1 to 25% by weight of antiperspirant active, (ii) 0.5 to 5% by weight of urea, (iii) a volatile propellant, and (iv) a non-ethanolic carrier oil, wherein the composition is free from ethanol.

In a second aspect the present invention provides an anhydrous base composition comprising: (i) 10 to 90% by weight of antiperspirant active, (ii) 2 to 15% by weight of urea, and (iii) a non-ethanolic carrier oil, wherein the composition is free from ethanol.

In a third aspect the present invention provides a process of manufacture an anhydrous antiperspirant aerosol composition as described in the first aspect, wherein the said manufacture comprises mixing the base composition as described in the second aspect to give a homogeneous, anhydrous dispersion, followed by diluting this dispersion with a volatile propellant.

In a fourth aspect the present invention provides a method of thickening an anhydrous base composition, said method comprising the incorporation of 2 to 15% by weight of urea to the mixture of a non-ethanolic carrier oil and 10 to 90% by weight of antiperspirant active. The present invention enables this method to be performed successfully without significantly increasing the risk of blockage.

In a fifth aspect the present invention provides a cosmetic method of simultaneously reducing perspiration and ameliorating skin de-moisturisation comprising topical application onto the skin a composition as described in the first aspect.

Herein, ameliorating skin de-moisturisation refers to easing or reducing the drying or dryness of the skin, particularly in the underarm regions of the human body. Underarm skin may be prone to skin problems because of a variety of causes, for example, shaving or depilating of underarm hair irritates the skin and can result in reduction in the moisture content of the stratum corneum. Ameliorating skin de-moisturisation can also mean improvement of the moisturisation level of the skin and improvement of the skin barrier properties.

These and other aspects, features and advantages will become apparent to those of ordinary skill in the art from a reading of the following detailed description and the appended claims. For the avoidance of doubt, any feature of one aspect of the present invention may be utilised in any other aspect of the invention.

The word "comprising" is intended to mean "including" but not necessarily "consisting of" or "composed of." In other words, the listed steps or options need not be exhaustive.

It is noted that the examples given in the description below are intended to clarify the invention and are not intended to limit the invention to those examples per se.

All percentages are weight/weight percentages and ratios are ratios by weight, unless otherwise indicated. Except in the operating and comparative examples, or where otherwise explicitly indicated, all numbers in this description indicating amounts of material or conditions of reaction, physical properties of materials and/or use are to be understood as modified by the word "about". Numerical ranges expressed in the format "from x to y" are understood to include x and y. When for a specific feature multiple preferred ranges are described in the format "from x to y", it is understood that all ranges combining the different endpoints are also contemplated. Numeric ranges expressed in the form "between x and y" are understood to include x and y.

Preferences expressed with regard to compositions also apply to the use of the composition for achieving antiperspirancy.

DETAILED DESCRIPTION OF THE INVENTION

Antiperspirant aerosol compositions according to the invention comprise two parts, a first part that is an anhydrous base composition comprising all the ingredients of the composition except the volatile propellant and a second part that is the volatile propellant.

The base and the aerosol compositions of the present invention are anhydrous, having less than 1% by weight of free water and preferably less than 0.1% by weight of free water.

Herein, "free water" excludes any water of hydration associated with the antiperspirant salt or other component added to a particular composition, but includes all other water present.

The base and the aerosol compositions of the present invention comprise a non-ethanolic carrier oil, i.e. a carrier oil other than ethanol.

The anhydrous aerosol composition and/or the anhydrous base composition is/are free from ethanol. With reference to the aerosol composition, this should be understood to mean that the composition has less than 1% ethanol, preferably less than 0.5% ethanol and most preferably is completely free from ethanol. With reference to the base composition, "free from ethanol" should be understood to mean that the composition has less than 2% ethanol, preferably less than 1% ethanol and most preferably is completely free from ethanol.

Antiperspirant Active

Antiperspirant actives for use in the composition of the present invention contain aluminium. They are typically astringent salts. Preferred salts are halohydrate salts, such as chlorohydrates.

Particularly suitable aluminium-containing actives are halohydrates defined by the general formula $Al_2(OH)_xQ_y \cdot wH_2O$ in which Q represents chlorine, bromine or iodine, x is variable from 2 to 5 and x+y=6 while $wH_2O$ represents a variable amount of hydration. Especially effective aluminium halohydrate salts are known as activated aluminium chlorohydrates and are made by methods known in the art.

Also preferred are aluminium salts comprising aluminium sesquichlorohydrate (ASCH) of chemical formula $Al_2OH_{4.4}Cl_{1.6}$ to $Al_2OH_{4.9}Cl_{1.1}$ Most commercial ASCH samples are of chemical formula $Al_2OH_{4.7}Cl_{1.3}$ to $Al_2OH_{4.9}Cl_{1.1}$ and these are further preferred.

Particularly preferred ASCH salts as described in the paragraph immediately above also comprise water-soluble calcium salt and amino acid, in particular glycine. Such salts are preferable of enhanced activity, achieved by heating the ASCH with the water-soluble calcium salt and amino acid at sufficient temperature and for sufficient time for the antiperspirancy performance of the ASCH to be improved. Further details on this technology may be found in WO 2014/187685 by Unilever.

Preferred antiperspirant actives are activated, that is to say, of enhanced efficacy. Such activated salts are typically prepared by procedures that reduce the water content of said salts.

Particularly preferred antiperspirant actives are aluminium chlorohydrates, activated aluminium chlorohydrates and activated aluminium sesquichlorohydrate.

The antiperspirant active is present in the aerosol composition in a concentration of 1 to 25%, preferably at least 2%, more preferably at least 4%, but typically not more than 20%, preferably not more than 15%, more preferably not more than 10%, by weight of the total composition.

The antiperspirant active is present in the base composition in a concentration of 10 to 90%, preferably at least 20%, more preferably at least 30%, but typically not more than 70%, preferably not more than 60%, more preferably not more than 50%, by weight of the base composition.

Urea

The composition according to the invention comprises urea. Urea is known as a humectant with a superior ability to absorb water.

Urea is present in the aerosol composition in a concentration of 0.5 to 5%, preferably at least 1%, but typically less than 4%, preferably less than 3% more preferably less than 2% by weight of the total composition.

Urea is present in the base composition in a concentration of 2 to 15%, preferably at least 2.5%, more preferably at least 3%, but typically less than 12%, preferably less than 10% by weight of the base composition.

Non-Ethanolic Carrier Oil

The anhydrous aerosol composition comprises a non-ethanolic carrier oil. In preferred embodiments, this may also be a masking oil, serving the purpose of reducing visible deposits when the composition accidentally comes into contact with clothing, for example.

Herein, the term "oil" signifies a water-insoluble organic material that is liquid at 20° C. Any material having a solubility of less than 0.1 g/100 g at 20° C. is considered to be insoluble.

A preferred optional component for use in accordance with the present invention is a fragrance oil, sometimes alternatively called a perfume oil. The fragrance oil may comprise a single fragrance or component more commonly a plurality of fragrance components. Herein, fragrance oils impart an odour, preferably a pleasant odour, to the composition. Preferably, the fragrance oil imparts a pleasant odour to the surface of the human body the composition is applied to the same.

The amount of fragrance oil in the aerosol composition is commonly up to 3% advantageously is at least 0.5% and particularly from 0.8% to 2%.

The total amount of non-ethanolic carrier oil in the aerosol composition is preferably from 0.1 to 20%, more preferably from 0.5 to 10%, and most preferably at from 2 to 8% by weight of the total composition. In certain preferred embodiments the carrier oil is present at greater than 2.5% and less than 6% by weight of the total composition.

The total amount of non-ethanolic carrier oil in the base composition is preferably 35 to 85%, more preferably at least 45% but typically not more than 75% and preferably not more than 65%.

The non-ethanolic carrier oil may be selected from any of those known in the art, although hydrophobic carrier oils are preferred.

Preferred carrier oils are silicone oils, that is to say, liquid polyorganosiloxanes. Such materials may be cyclic or linear, examples include Dow Corning silicone fluids 344, 345, 244, 245, 246, 556, and the 200 series; Union Carbide Corporation Silicones 7207 and 7158; and General Electric silicone SF1202. Suitable carrier oils can be selected from alkyl ether oils having a boiling point of above 100° C. and especially above 150° C., including polyalkyleneglycol alkyl ethers. Such ethers desirably comprise between 10 and 20 ethylene glycol or propylene glycol units and the alkyl group commonly contains from 4 to 20 carbon atoms. The preferred ether oils include polypropylene glycol alkyl ethers such as PPG-14-butylether and PPG-15-stearyl ether.

Suitable carrier oils can include one or more triglyceride oils. The triglyceride oils commonly comprise the alkyl residues of aliphatic $C_7$ to $C_{20}$ alcohols, the total number of carbon atoms being selected in conjunction with the extent of olefinic unsaturation and/or branching to enable the triglyceride to be liquid at 20° C. One example is jojoba oil. Particularly preferably, in the triglyceride oil the alkyl residues are linear $C_{18}$ groups having one, two or three olefinic degrees of unsaturation, two or three being optionally conjugated, many of which are extractable from plants (or their synthetic analogues), including triglycerides of oleic acid, linoleic acid, conjugated linoleic acids, linolenic acid, petroselenic acid, ricinoleic acid, linolenelaidic acid, trans 7-octadecenoic acid, parinaric acid, pinolenic acid, punicic acid and stearidonic acid.

Suitable carrier oils can include those derived from unsaturated $C_{18}$ acids, including coriander seed oil, impatiens balsimina seed oil, parinarium laurinarium kernel fat oil, sabastiana brasilinensis seed oil, dehydrated castor seed oil, borage seed oil, evening primrose oil, aquilegia vulgaris oil, sunflower (seed) oil and safflower oil. Other suitable oils are obtainable from hemp, and maize corn oil. An especially preferred oil by virtue of its characteristics is sunflower (seed) oil.

Further suitable carrier oils, that can also be emollient oils, comprise alkyl or alkyl-aryl ester oils having a boiling point of above 150° C. (and a melting point of below 20° C.). Such ester oils include oils containing one or two alkyl groups of 12 to 24 carbon atoms length, including isopropyl myristate, isopropyl palmitate and myristyl palmitate. Other non-volatile ester oils include alkyl or aryl benzoates such $C_{12-15}$ alkyl benzoate, for example Finsolv TN™ or Finsolv Sun™.

A further class of suitable carrier oils comprises non-volatile dimethicones, often comprising phenyl or diphenylene substitution, for example Dow Corning 200 350 cps or Dow Corning 556.

Volatile Propellant

The present anhydrous aerosol antiperspirant composition comprises a volatile propellant that is typically a liquefied propellant gas. Preferred liquefied propellant gases are hydrocarbons or halogenated hydrocarbon gases (particularly fluorinated hydrocarbons such as 1,1-difluoroethane and/or 1-trifluoro-2-fluoroethane) that have a boiling point of below 10° C. and especially those with a boiling point below 0° C. It is especially preferred to employ liquefied hydrocarbon gases, and especially $C_3$ to $C_6$ hydrocarbons, including propane, butane, isobutane, pentane and isopentane and mixtures of two or more thereof. Of these especially preferred propellants, isobutane, isobutane/propane, butane/propane and mixtures of propane, isobutane and butane are most preferred.

The liquefied propellant gas is typically the major component of aerosol compositions according to the invention, often comprising from 30 to 99% weight, preferably comprising from 40 to 95% by weight and even more preferably from 70 to 90% by weight.

Other Components

Other non-essential components may also be including in compositions according to the invention. A suspending agent is a highly preferred component of compositions of the invention. Such agents aid the suspension of the particulate antiperspirant active system in the composition. Preferred suspending agents are clays, particularly hydrophobically modified clays. Particularly preferred are hydrophobically modified hectorite or bentonite clays and especially preferred is disteardimonium hectorite (e.g. Bentone 38V, ex Elementis).

The suspending agent is typically employed at from 0.1 to 1.5% by weight of the total aerosol composition.

Propylene carbonate may also be advantageously employed in compositions of the present invention, typically at from 0.001 to 0.1% by weight.

It is preferred that the base composition has a viscosity of less than 10000 cPs (mPa·s), preferably between 2000 and 10000 cPs (mPa·s), more preferably between 2000 and 8000 cPs (mPa·s), still more preferably between 2500 and 7500 cPs (mPa·s), most preferably between 2600 and 7000 cPs (mPa s), all at 10 rpm.

Herein, viscosity is measured at 20° C. using a Brookfield Viscometer 24 hours after sample preparation, using a $T_A$ spindle, at 10 rpm.

When the base composition has a viscosity of less than 10000 cPs (mPa·s), urea is present in the base composition in a concentration of 3 to 12%, preferably 3.5 to 11.6% by weight of the base composition.

Herein, unless stated otherwise, the particle size and distributions are those obtained by laser light scattering, for example obtained from the appropriate Mastersizer instrument for anhydrous suspensions, obtainable from Malvern instruments and set to produce a volume plot. The instrument is employed with lens selected in accordance with the maker's instructions to accommodate the expected particle size distribution, (or various lenses can be tested until the best lens is identified) and is preferably operated employing cyclomethicone PMX-0245 as the liquid dispersant for a sample of the base composition to attain a particles concentration that achieves obscuration, i.e. 10 to 30% light scattered. Using the polydisperse analysis model and knowing the dispersant RI, the RI of the particulate material and imaginary RI factor of 0.1, the plot of the particles size (D) distribution and the average particle size d50 is obtained.

The particle size of the feedstock aluminium chlorohydrate, be it activated, complexed or otherwise, desirably have a diameter of below 125 microns, preferably at least 95% by weight below 100 microns and especially at least 95% by weight below 75 microns. There is a tendency for the particle size distribution of the particulate antiperspirant salt to be altered by blending it with a humectant in a non-ethanolic hydrophobic carrier fluid. Advantageously by selection of urea, the effect on size increase is markedly less than for glycerol and PEG-4. It will also be recognized that the effect can be controlled by a suitable selection of urea, in combination with the amount of its incorporation. It is particularly advantageous to control those two parameters together with the particulate antiperspirant feedstock, such that the particle size of the solid particles present in the composition of the present invention should not be greater than 125 μm, preferably not greater than 100 μm, more preferably not greater than 80 μm or even not greater than 50 μm Manufacture During manufacture of an aerosol antiperspirant product, the base composition is made by mixing together all the composition ingredients other than the propellant, agitating the mixture to suspend the particulate antiperspirant in the carrier liquid, introducing the mixture into an aerosol canister, fitting an outlet delivery line to the canister, sealing the canister and finally pressurising the canister by introduction of the propellant.

The canister can be made from tin plate or aluminium. The discharge line includes a valve biased to the closed position, and may be a depression or tilt valve, i.e. the valve can be opened by depression or lateral movement. The discharge line terminates in a spray nozzle. The nozzle outlet has an internal diameter that is usually selected within the range of from 300 to 800 microns, particularly not greater than 600 microns and in many embodiments from 350 to 450 microns. This is particularly beneficial that it enables the composition to be sprayed without an undue risk of blockage through nozzles of similar internal diameter currently employable with corresponding otherwise similar compositions that lack the urea.

The invention will now be illustrated by means of the following non-limiting examples.

EXAMPLES

Example 1: Evaluation of Urea on its Ability to Absorb Water

In this example, urea and other commonly used humectants were evaluated in terms of their ability to absorb water as a function of relative humidity, at a given temperature, using Dynamic Vapour Sorption instrument (Surface Measurement Systems), in which the (water) vapour concentration surrounding the sample can be varied and change in mass followed over time, for a given temperature, using a microbalance. In order for experimental conditions to mimic the environment in the axilla, the materials were evaluated at 37° C., with a relative humidity range from 30% to 90%.

| INCI Name (Trade Name) | Supplier | Supplied as | % Change in Mass, DVS (37° C. 90% RH) |
|---|---|---|---|
| Glycerin (Palmera G995v) | KLK Oleo | Liquid | 105.14 |
| PEG 4 (Polyglykol 200 USP) | Clariant | Liquid | 66.68 |
| Panthenol (Surfac DL) | Surfachem | Free flowing particulate | 35.77 |
| Urea | Sigma-Aldrich | Free flowing particulate | 142.16 |

The above example shows that urea is superior in its ability to absorb water when compared to any of the other commonly used humectants.

Example 2: Effect of Urea on the Agglomeration of an Anhydrous Antiperspirant Base Composition This example demonstrates the effect of urea (Ex 1) on the stability of an anhydrous antiperspirant composition when compared to other commonly used humectants (Comp A to Comp C)

Preparation of the Compositions

The antiperspirant active, AACH 7172, was added to a beaker containing the cosmetic oils, Fluid AP, PMX-0245 and Finsolv TN. Contents of beaker were sheared at 6000 rpm, for at least 5 minutes, using high shear mixer (Silverson L4RT), fitted with 1" head. Humectant was added to the beaker containing the antiperspirant active and the cosmetic oils. Contents of beaker were then sheared for a further 2 minutes.

Once prepared, the resultant model aerosol base formulation was visually assessed for signs of agglomeration.

| Set | INCI Name | Trade Name | Wt % Comp A | Comp B | Comp C | Ex 1 |
|---|---|---|---|---|---|---|
| Antiperspirant active | Aluminum Chlorohydrate | AACH 7172 | 46.09 | 46.09 | 46.09 | 46.09 |
| Cosmetic oils | PPG-14 Butyl Ether | Fluid AP | 26.65 | 26.65 | 26.65 | 26.65 |
|  | Cyclopentasiloxane | PMX-0245 | 18.04 | 18.04 | 18.04 | 18.04 |
|  | C12-15 Alkyl Benzoate | Finsolv TN | 4.61 | 4.61 | 4.61 | 4.61 |
| Humectant | Glycerin | Palmera G995v (ex KLK Oleo) | 4.61 | — | — | — |
|  | PEG 4 | Polyglykol 200 USP (ex Clariant) | — | 4.61 | — | — |
|  | Panthenol | Surfac D (ex Surfachem) | — | — | 4.61 | — |
|  | Urea | Sigma-Aldrich | — | — | — | 4.61 |
| Stability (in terms of agglomeration) | — | — | Apparent agglomeration | Apparent agglomeration | No apparent agglomeration | No apparent agglomeration |

It is apparent from the above table that the composition according to the invention (Ex 1) is better than any of the other compositions which use a humectant other than urea. Even though glycerine has a high ability to absorb water as evidenced from Example 1, in an anhydrous composition it agglomerates with the antiperspirant active. Panthenol, on the other hand, results in a stable composition; however, it is inferior in its ability to absorb water.

Example 3: Effect of Concentration of Urea on the Viscosity and Particle Size of the Anhydrous Antiperspirant Base Composition In this example, different concentrations of urea in accordance with the invention (Ex 2 to Ex 4) are compared with a Control and comparative composition (Comp D).

For this study, urea was incorporated into the below base formulation in different concentrations. % w/w PMX-0245 was adjusted accordingly.

| INCI Name | Trade Name | % w/w Full Formulation | Base Formulation |
|---|---|---|---|
| Butane, Isobutane, Propane | AP40 | 87.000 | — |
| Aluminum Chlorohydrate | AACH 7172 | 5.000 | 38.462 |
| PPG-14 Butyl Ether | Fluid AP | 2.891 | 22.238 |
| Cyclopentasiloxane | PMX-0245 | 2.456 | 18.892 |
| Parfum | Parfum | 0.650 | 5.000 |
| Disteardimonium Hectorite | Bentone 38v | 0.550 | 4.231 |
| *Helianthus annuus* Seed Oil | Akosun | 0.520 | 4.000 |
| C12-15 Alkyl Benzoate | Finsolv TN | 0.500 | 3.846 |
| Cyclopentasiloxane and Dimethiconol | DC1501 | 0.200 | 1.538 |
| Octyldodecanol | Eutanol G | 0.117 | 0.900 |
| BHT | Tenox BHT | 0.100 | 0.769 |
| Propylene Carbonate | Propylene Carbonate | 0.015 | 0.115 |
| Vitamin E Acetate | Vitamin E Acetate Care | 0.001 | 0.008 |

Preparation of the Compositions

The cosmetic oils, PMX-0245 and DC1501, were weighed into appropriately sized beaker and mixed with the aid of a spatula. The other cosmetic oils in the formulation, Fluid AP, Akosun, Finsolv TN and Eutanol G, were each added to the beaker and the contents mixed with the aid of a spatula. The preservative, Tenox BHT, was added to the beaker. Contents of beaker were sheared at 6000 rpm, for 1 minute, using high shear mixer (Silverson L4RT), fitted with 1" head. The structurant, Bentone 38v, was added to beaker, and in order to 'wet out' the powders the contents of beaker were mixed with the aid of a spatula. Contents of beaker were sheared at 6000 rpm, for 2 minutes to separate the Bentone platelets. The polar activators, propylene carbonate and fragrance were added and contents of beaker sheared at 6000 rpm for a further 3 minutes. The antiperspirant active (APA), AACH 7172 was added slowly, in stages. Contents of beaker were mixed after each addition with the aid of spatula. Contents of beaker sheared at 6000 rpm for at least 5 minutes.

Prior to its use, urea was passed through a 100 μm sieve. Urea was added to the beaker and the contents mixed with a spatula. The contents of the beaker were sheared at 6500 rpm for a further two minutes, prior to pouring resultant aerosol base formulation into a suitable container.

Particle size of each of the APA base formulations was measured using Malvern Mastersizer 2000, 24 hours after their preparation. Each of the formulations were shaken for at least 10 seconds prior to pre-dispersing the APA base in PMX-0245 before adding resultant dispersion to the small volume sample dispersion unit containing PMX-0245.

| Formulation Details | % w/w urea in APA aerosol Formulation | Viscosity (cPs/mPas) 24 hrs after prep | D[4,3] - μm | d50 - μm | % Particles >125 μm |
|---|---|---|---|---|---|
| Control APA Base | — | 1960 | 26.853 ± 0.379 | 24.274 ± 0.255 | — |
| Ex 2 APA Base with 3.846% w/w urea | 0.5 | 2740 | 28.444 ± 0.532 | 25.853 ± 0.441 | — |
| Ex 3 APA Base with 7.692% w/w urea | 1.00 | 4180 | 33.103 ± 0.043 | 29.747 ± 0.043 | — |
| Ex 4 APA Base with 11.538% w/w urea | 1.50 | 7380 | 33.360 ± 0.151 | 30.276 ± 0.137 | — |
| Comp D APA Base with 15.385% w/w urea | 2.00 | 15560 | 37.026 ± 0.151 | 33.434 ± 0.156 | — |

The above table shows that the desired viscosity is obtained for base compositions with a urea concentration within the scope of the present invention (Ex 2 to Ex 4) when compared to a control sample without any urea. Comp D has urea in a concentration of more than 15% % by weight in the base composition. Its viscosity is exceeding the preferred range and close towards the margin of acceptability of ease of processing.

It is also obvious the particle size increases along the increase of urea concentration. Comp D has the largest D50 and d[4,3] although its particle size is acceptable by the present invention.

The invention claimed is:

1. A base composition for an antiperspirant aerosol comprising:
   a) less than 0.1% by weight of free water,
   b) 20 to 50% by weight of antiperspirant active that is an aluminium halohydrate salt,
   c) 2 to 15% by weight of urea, and
   d) 35 to 65% by weight of a non-ethanolic carrier oil selected from the group consisting of silicone oils, alkyl ether oils, triglycerides, ester oils, and mixtures thereof,
   wherein the non-ethanolic carrier oil is a water insoluble organic material that is liquid at ° C.,
wherein the base composition is free of ethanol and further wherein the base composition has a viscosity of less than or equal to 10000 cPs (mPa·s) measured at ° C. using a Brookfield Viscometer 24 hours after sample preparation, using a $T_A$ spindle, at 10 rpm, and further wherein urea possesses a % change in mass value measured at 37° C. and 90% relative humidity using Dynamic Vapour Sorption instrument greater than or equal to the value for PEG-4.

2. The base composition according to claim 1, comprising 3 to 12% by weight of urea.

3. The base composition according to claim 1 having a viscosity of between 2500 and 7500 cPs (mPa·s).

4. The base composition according to claim 1, wherein the aluminium halohydrate salt is aluminium sesquichlorohydrate having a chemical formula $Al_2OH_{4.4}Cl_{1.6}$ to $Al_2OH_{4.9}Cl_{1.1}$ and further comprising water-soluble calcium salt and amino acid.

5. The base composition according to claim 1, wherein the non-ethanolic carrier oil is a volatile silicone oil.

6. The base composition according to claim 1, further comprising a suspending agent.

7. The base composition according to claim 6, wherein the suspending agent comprises hydrophobically modified clays.

8. The base composition according to claim 1, comprising 30 to 50% by weight of antiperspirant active.

9. The base composition according to claim 1, wherein the aluminium halohydrate salt comprises aluminium chlorohydrate, activated aluminium chlorohydrate, activated aluminium sesquichlorohydrate or a mixture thereof.

10. The base composition according to claim 1, wherein the antiperspirant active is activated.

11. The base composition according to claim 1, comprising 45 to 65% by weight of non-ethanolic carrier oil.

12. The base composition according to claim 1 having a viscosity of between 2600 and 7000 cPs (mPa·s).

13. The base composition according to claim 1 having a particle size not greater than 125 μm.

14. The base composition according to claim 1 having a particle size not greater than 100 μm.

* * * * *